United States Patent
Fokoue-Nkoutche et al.

(10) Patent No.: US 10,783,997 B2
(45) Date of Patent: Sep. 22, 2020

(54) PERSONALIZED TOLERANCE PREDICTION OF ADVERSE DRUG EVENTS

(71) Applicant: INTERNATIONAL BUSINESS MACHINES CORPORATION, Armonk, NY (US)

(72) Inventors: Achille B. Fokoue-Nkoutche, White Plains, NY (US); Oktie Hassanzadeh, Port Chester, NY (US); Mohammad S. Hamedani, Chappaqua, NY (US); Meinolf Sellmann, Cortlandt Manor, NY (US); Ping Zhang, White Plains, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 964 days.

(21) Appl. No.: 15/248,734

(22) Filed: Aug. 26, 2016

(65) Prior Publication Data
US 2018/0060508 A1    Mar. 1, 2018

(51) Int. Cl.
*G16H 20/10*    (2018.01)
*G16H 70/40*    (2018.01)
(Continued)

(52) U.S. Cl.
CPC ............. *G16H 50/20* (2018.01); *G16H 15/00* (2018.01); *G16H 20/10* (2018.01); *G16H 70/40* (2018.01)

(58) Field of Classification Search
CPC ........ G16H 50/20; G16H 15/00; G16H 70/40; G16H 20/10; H06F 19/00; H06F 19/30;
(Continued)

(56) References Cited

U.S. PATENT DOCUMENTS

2003/0178031 A1*  9/2003  Du Pen ................ A61B 5/00
                                                     128/898
2007/0037198 A1   2/2007  Cox et al.
(Continued)

FOREIGN PATENT DOCUMENTS

WO    2009108802 A2    9/2009

OTHER PUBLICATIONS

Fokoue et al., "Predicting Drug-Drug Interactions Through Similarity-Based Link Prediction Over Web Data," WWW 2016, 4 pages.
Fokoue et al., "Tiresias: Knowledge Engineering and Large-Scale Machine Learning for Interpretable Drug-Drug Interaction Prediction," In proceedings of the American Medical Informatics Association Annual Symposium; 1 page, AMIA 2016.
(Continued)

*Primary Examiner* — Elaine Gort
*Assistant Examiner* — Christopher B Wehrly
(74) *Attorney, Agent, or Firm* — Cantor Colburn LLP; Anthony Curro

(57) ABSTRACT

Embodiments include method, systems and computer program products for predicting adverse drug events on a computational system. Aspects include receiving a personalized data set including a plurality of real-time drug doses for a first drug or drug combination and a plurality of corresponding real-time adverse drug reaction tolerance data for the first drug or drug combination for a patient. Aspects also include receiving known drug data for a candidate drug or drug pair. Aspects also include calculating, based upon the known drug data and the personalized data set, a predicted adverse drug reaction tolerance for the candidate drug or drug pair at a candidate dosage, wherein the predicted adverse drug reaction tolerance is personalized to the patient.

18 Claims, 6 Drawing Sheets

(51) Int. Cl.
*G16H 50/20* (2018.01)
*G16H 15/00* (2018.01)

(58) Field of Classification Search
CPC ...... H06F 19/32; H06F 19/34; H06F 19/3456; G06Q 50/22; G06Q 50/24
USPC .......................................................... 705/3
See application file for complete search history.

(56) References Cited

U.S. PATENT DOCUMENTS

| | | |
|---|---|---|
| 2009/0076857 A1 | 3/2009 | Eletreby et al. |
| 2009/0171697 A1* | 7/2009 | Glauser .................. G01N 33/94 705/3 |
| 2012/0209625 A1 | 8/2012 | Armstrong et al. |
| 2012/0221376 A1 | 8/2012 | Austin |
| 2013/0179187 A1 | 7/2013 | Jackson et al. |
| 2014/0058741 A1 | 2/2014 | Bronn |
| 2014/0156304 A1 | 6/2014 | Michon et al. |
| 2014/0343958 A1 | 11/2014 | Heard |
| 2014/0350954 A1 | 11/2014 | Ellis et al. |

OTHER PUBLICATIONS

Fokoue, et al., "Predicting Drug-Drug Interactions through Large-Scale Similarity-Based Link Prediction," ESWC (2016), 15 pages.

Luo et al., "DDI-CPI, a Server that Predicts Drug-Drug Interactions Through Implementing the Chemical-Protein Interactome," Nucleic Acids Research, p. gku433 (2014), 7 pages.

Sadoghi et al., "Self-Curating Databases," 19th International Conference on Extending Database Technology, Mar. 15-18, 2016, pp. 467-472.

Vilar et al., "Detection of Drug-Drug Interactions by Modeling Interaction Profile Fingerprints," PloS One (8(3), e58321 (2013), 11 pages.

Vilar et al., "Similarity-Based Modeling in Large-Scale Prediction of Drug-Drug interactions," Nature Protocols 9(9) (2014); pp. 2147-2163.

Zhang et al., "Towards Personalized Medicine: Leveraging Patient Similarity and Drug Similarity Analytics" AMIA Summits on Translational Science Proceedings 2014, 5 pages.

\* cited by examiner

PERSONALIZED TOLERANCE PREDICTION OF ADVERSE DRUG EVENTS

BACKGROUND

The present disclosure relates to personalized prediction of adverse drug reaction on computational systems and more specifically, to methods, systems and computer program products for analysis of data to provide personalized prediction of patient tolerance of adverse drug events for a candidate drug at a candidate dosage based upon collected real-time data on computational systems.

Adverse drug events pose several challenges to the healthcare system. It has been estimated that over 2 million serious adverse drug events occur yearly and as many as 100,000 related deaths may occur each year as a result. Adverse drug events are a leading cause of death ahead of pulmonary disease, diabetes, AIDS, accidents and automobile deaths and are believed to be responsible for as many as one in five injuries or deaths in hospitalized patients. Moreover, the yearly cost associated with adverse drug events is estimated at $136 billion dollars, which is higher than costs associated with diabetic and cardiovascular care. Moreover, the tolerance of an individual patient to an adverse event can play a role in the treatment of that patient. For example, a patient with a higher tolerance to an adverse event could in some cases be administered a higher dosage of a medication, thereby potentially increasing the patient's treatment outcome and quality of life.

SUMMARY

In accordance with one or more embodiments, a computer-implemented method for determining an adverse reaction drug tolerance includes receiving to a processor, a personalized data set comprising a plurality of real-time drug doses for a first drug or drug combination and a plurality of corresponding real-time adverse drug reaction tolerance data for the first drug or drug combination for a patient. The method also includes receiving, to the processor, known drug data for a candidate drug or drug pair. The method also includes calculating, by the processor, based upon the known drug data and the personalized data set, a predicted adverse drug reaction tolerance for the candidate drug or drug pair at a candidate dosage, wherein the predicted adverse drug reaction tolerance is personalized to the patient.

In accordance with one or more embodiments, a computer program product for calculating an adverse reaction drug tolerance on a computational system is provided. The computer program product includes a computer readable storage medium having program instructions embodied therewith, the program instructions executable by a processor to cause the processor to receive a personalized data set comprising a plurality of real-time drug doses for a first drug or drug combination and a plurality of corresponding real-time adverse drug reaction tolerance data for the first drug or drug combination for a patient. The processor also receives a personalized data set comprising a plurality of real-time drug doses for a first drug or drug combination and a plurality of corresponding real-time adverse drug reaction tolerance data for the first drug or drug combination for a patient. The processor also calculates, based upon the known drug data and the personalized data set, a predicted adverse drug reaction tolerance for the candidate drug or drug pair at a candidate dosage, wherein the predicted adverse drug reaction tolerance is personalized to the patient.

In accordance with one or more embodiments, a processing system for calculating an adverse reaction drug tolerance on a computational system includes a processor in communication with one or more types of memory. The processor is configured to receive a personalized data set comprising a plurality of real-time drug doses for a first drug or drug combination and a plurality of corresponding real-time adverse drug reaction tolerance data for the first drug or drug combination for a patient. The processor is also configured to receive known drug data for a candidate drug or drug pair. The processor is also configured to calculate, based upon the known drug data and the personalized data set, a predicted adverse drug reaction tolerance for the candidate drug or drug pair at a candidate dosage, wherein the predicted adverse drug reaction tolerance is personalized to the patient.

BRIEF DESCRIPTION OF THE SEVERAL VIEWS OF THE DRAWINGS

The subject matter of the present disclosure is particularly pointed out and distinctly claimed in the claims at the conclusion of the specification. The foregoing and other features and advantages of the one or more embodiments disclosed herein are apparent from the following detailed description taken in conjunction with the accompanying drawings in which:

DETAILED DESCRIPTION

Figure 1:
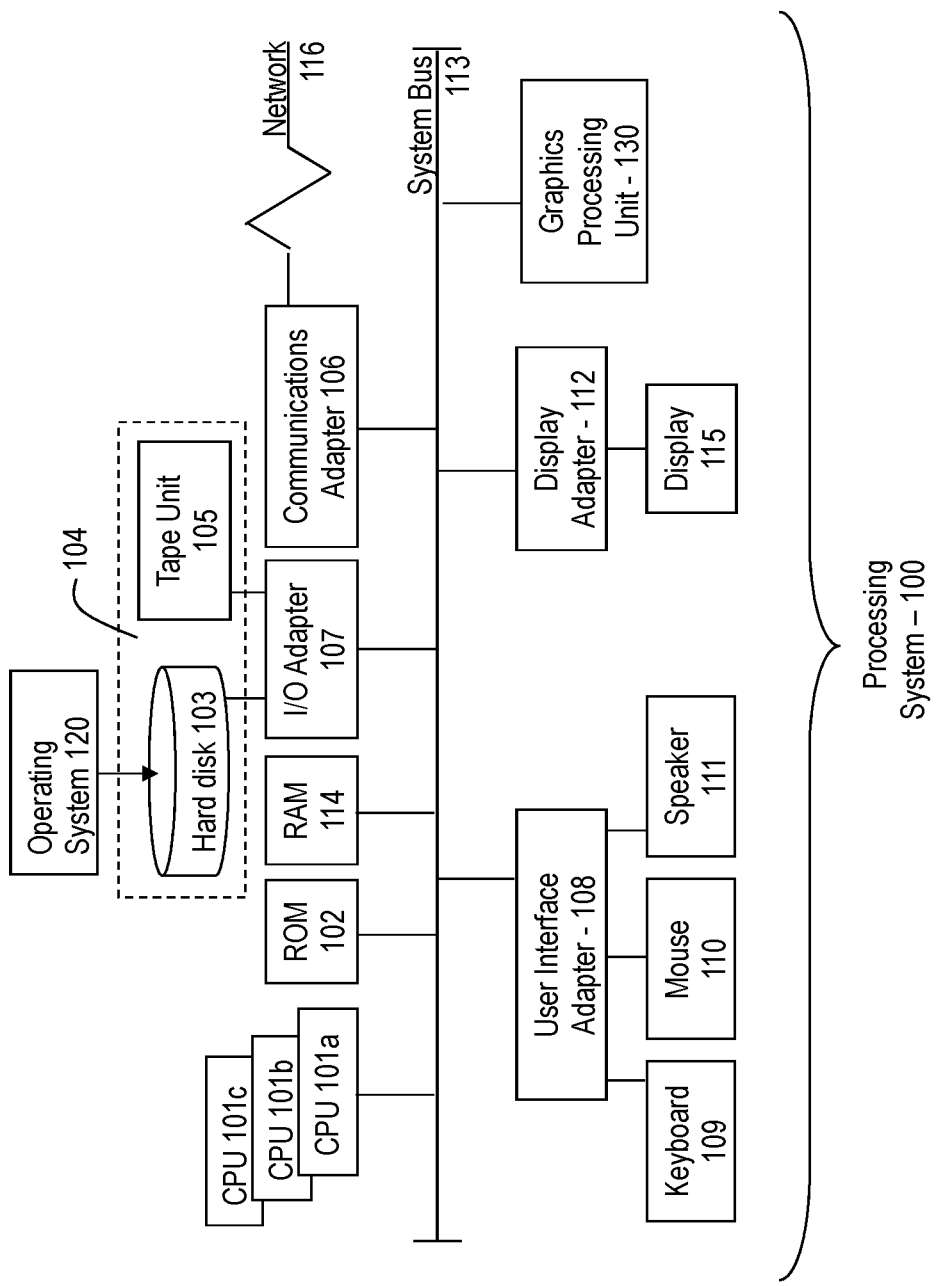
FIG. 1 is a block diagram illustrating one example of a processing system for practice of the teachings herein.

In accordance with exemplary embodiments of the disclosure, methods, systems and computer program products for personalized medication adjustment are provided. Embodiments include predicting adverse drug reactions while balancing drug efficacy and patient tolerance to the adverse drug reactions. Methods, systems, and computer program products can include monitoring patients in real-time and refining a regression model accordingly, for example to provide personalize medication adjustment.

Publicly available adverse drug reaction databases are primarily used for storing known adverse drug reactions for a single drug or combination of drugs. Such databases can be limited to containing only known adverse drug events and can lack the capability to predict other plausible adverse drug reactions that have yet to be reported or experienced. In addition, such databases fail to incorporate the specific circumstances under which a drug was taken and many personalized patient data (including, for instance, patient medical history, demographic data, genetic information, etc.) even though such circumstances and data may contribute to the undesirable adverse drug reaction. In addition, adverse drug reaction databases can overlook the efficacy of treatment and willingness of a patient to tolerate the adverse drug reactions in order to treat his or her condition. Moreover, adverse drug reaction databases can be static in nature and do not receive sensor information on adverse drug reactions in-time from patients under treatment. Real-time feedback can be beneficial in patient treatment, and is, for example, essential for distinguishing between short term and long-term reactions and treatment needs. The length of treatment and the duration of adverse drug reactions can factor into whether a patient can tolerate such adverse drug reactions.

Public databases contain a variety of information regarding known drugs, including chemical structural data and chemical data. These information sources may contain structured or unstructured data. For example, scientific literature may report results or observations related to known drugs in either a non-clinical or a clinical setting in a narrative document. For example, a physician may report an observation of an individual adverse event experience by a patient, or a chemist may surmise that a given drug operates by a particular mechanism given its chemical structure. However, the compilation and analysis of such data has remained complicated by the lack of structure in such reporting. Moreover, many databases contain incomplete data for a given drug, and it thus can be difficult to computationally distinguish between a missing datum, for example when it is not known if a drug in question contains a particular feature, and a negative event, such as when a drug is known not to have that particular feature. In addition, such public sources generally lack personalized information, such as demographic or genomic information or information concerning patient tolerance to adverse events that might reveal potential adverse events and potential tolerance levels for adverse events for candidate drugs or for individual candidate patients.

The methods, systems, and computer program products described herein can provide a model including real-time monitoring to predict adverse drug event tolerance or severity, allowing adjustment of medications or medication dosages. In addition, a prediction model can be continuously refined based upon real-time information, such as through sensor and a patient reporting mechanism, in addition to leveraging known static adverse drug reaction databases.

Referring to FIG. 1, there is shown an embodiment of a processing system 100 for implementing the teachings herein. In this embodiment, the system 100 has one or more central processing units (processors) 101a, 101b, 101c, etc. (collectively or generically referred to as processor(s) 101). In one embodiment, each processor 101 may include a reduced instruction set computer (RISC) microprocessor. Processors 101 are coupled to system memory 114 and various other components via a system bus 113. Read only memory (ROM) 102 is coupled to the system bus 113 and may include a basic input/output system (BIOS), which controls certain basic functions of system 100.

FIG. 1 further depicts an input/output (I/O) adapter 107 and a network adapter 106 coupled to the system bus 113. I/O adapter 107 may be a small computer system interface (SCSI) adapter that communicates with a hard disk 103 and/or tape storage drive 105 or any other similar component. I/O adapter 107, hard disk 103, and tape storage device 105 are collectively referred to herein as mass storage 104. Operating system 120 for execution on the processing system 100 may be stored in mass storage 104. A network adapter 106 interconnects bus 113 with an outside network 116 enabling data processing system 100 to communicate with other such systems. A screen (e.g., a display monitor) 115 is connected to system bus 113 by display adaptor 112, which may include a graphics adapter to improve the performance of graphics intensive applications and a video controller. In one embodiment, adapters 107, 106, and 112 may be connected to one or more I/O busses that are connected to system bus 113 via an intermediate bus bridge (not shown). Suitable I/O buses for connecting peripheral devices such as hard disk controllers, network adapters, and graphics adapters typically include common protocols, such as the Peripheral Component Interconnect (PCI). Additional input/output devices are shown as connected to system bus 113 via user interface adapter 108 and display adapter 112. A keyboard 109, mouse 110, and speaker 111 all interconnected to bus 113 via user interface adapter 108, which may include, for example, a Super I/O chip integrating multiple device adapters into a single integrated circuit.

In exemplary embodiments, the processing system 100 includes a graphics processing unit 130. Graphics processing unit 130 is a specialized electronic circuit designed to manipulate and alter memory to accelerate the creation of images in a frame buffer intended for output to a display. In general, graphics processing unit 130 is very efficient at manipulating computer graphics and image processing, and has a highly parallel structure that makes it more effective than general-purpose CPUs for algorithms where processing of large blocks of data is done in parallel.

Thus, as configured in FIG. 1, the system 100 includes processing capability in the form of processors 101, storage capability including system memory 114 and mass storage 104, input means such as keyboard 109 and mouse 110, and output capability including speaker 111 and display 115. In one embodiment, a portion of system memory 114 and mass storage 104 collectively store an operating system such as the AIX® operating system from IBM Corporation to coordinate the functions of the various components shown in FIG. 1.

Figure 2:
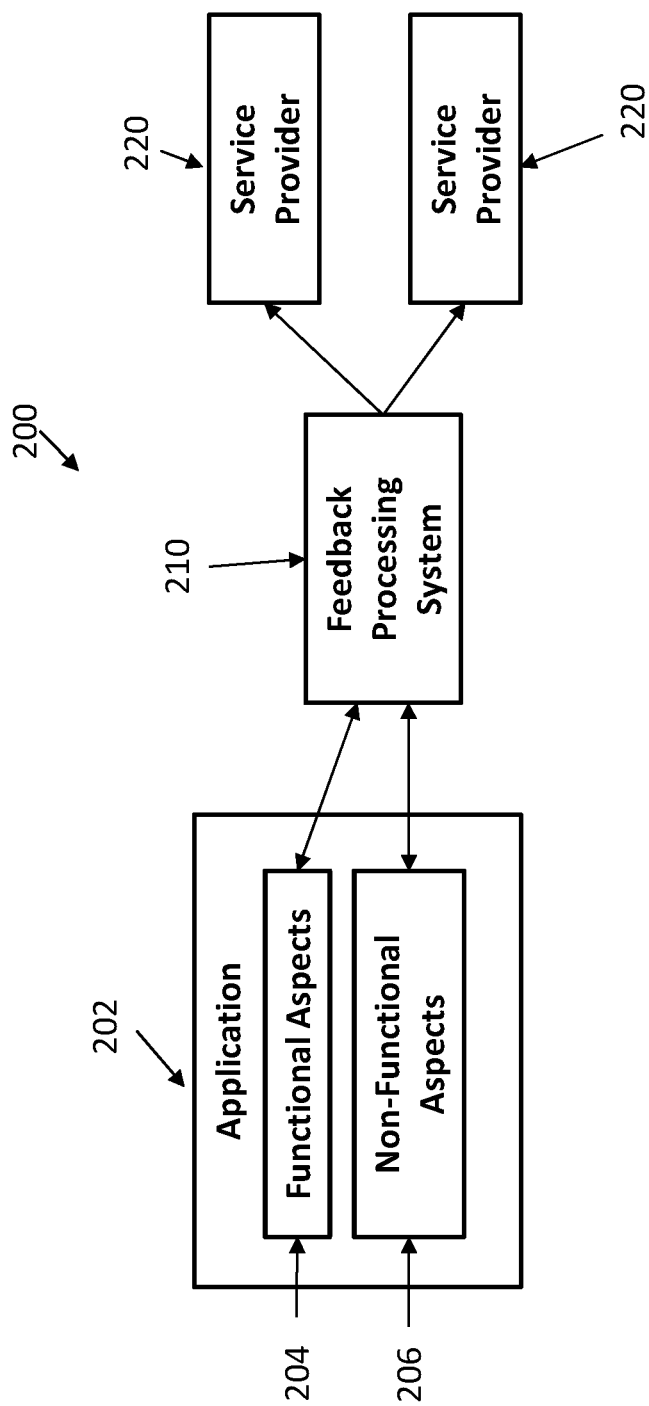
FIG. 2 is a block diagram illustrating a distributed computational system in accordance with one or more embodiments.

Referring now to FIG. 2, a distributed computational system 200 in accordance with one or more embodiments is illustrated. As illustrated, the distributed computational system 200 includes an application 202 which includes both functional objects 204 and non-functional objects 206. In one embodiment, the application 202 may be a website and the functional object 204 is an object, or part, of the website that a user interacts with. For example, the functional object 204 may be a search function on the web site, a find a store location of the website, a hyperlink on the website, an ordering function of the website, or the like. In exemplary embodiments, the application 202 may also include non-functional objects 206 that are aspects of the application 202 that the user does not directly interact with but which are utilized by the application 202. Such non-functional objects 206 may include JavaScripts, security features, user tracking features, and the like.

As illustrated, the distributed computational system 200 includes multiple service providers 220. In exemplary embodiments, each of the service providers 220 are associated with at least one of the functional objects 204 and the non-functional objects 206 of the application 202. The distributed computational system 200 also includes a feedback processing system 210 that is configured to receive feedback on the functional objects 204 and the non-functional objects 206 of the application 202 and to responsively provide feedback to the appropriate service provider 220. In exemplary embodiments, the feedback processing system 210 may be a processing system such as the one shown in FIG. 1.

Figure 3:
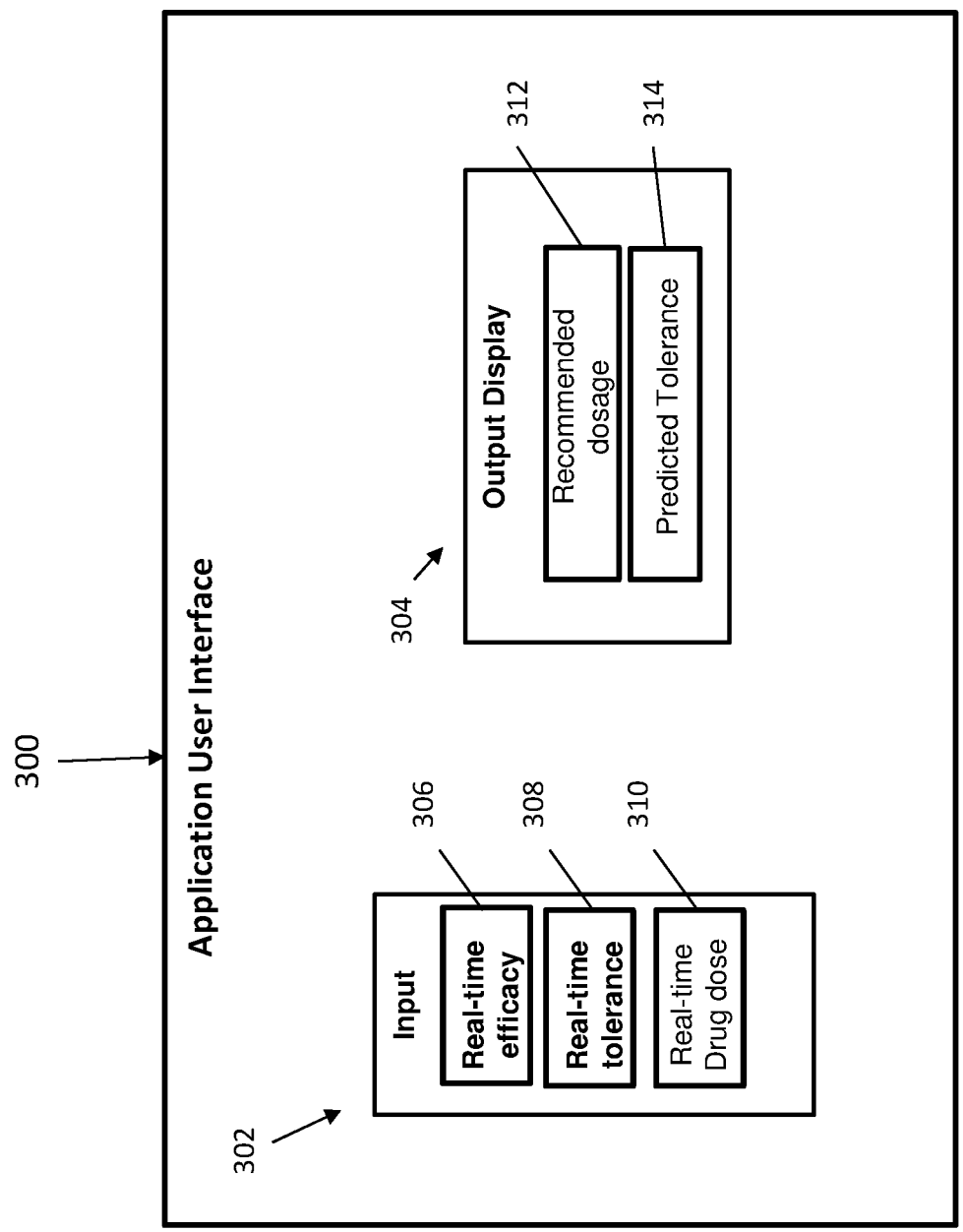
FIG. 3 is a schematic diagram illustrating a user interface of an application providing personalized predictions of tolerance to adverse events for a candidate patient in accordance with one or more embodiments.

Referring now to FIG. 3, a schematic of an application user interface 300 of an application in accordance with one or more embodiments is illustrated. As illustrated the application user interface 300 includes an input 302 and an output 304. In exemplary embodiments, the user may provide information at input 302 on an application user interface. In exemplary embodiments, the input can include real-time efficacy data 306. In some embodiments, the input 302 includes real-time tolerance data 308. In some embodiments, the input 302 can include real-time drug dosage data 310. In one embodiment, the input 302 may be configured to allow free form input, i.e., unstructured textual input from the user. In another embodiment, the input 302 may present the user with a window containing one or more multiple choice questions that allow the user to select from a series of tolerance options. For instance, an input can prompt a patient to rate their tolerance to an adverse reaction on a scale of 1-10. In some embodiments, the input can by provided by a patient or a health care provider or can be provided by a sensor. For example, input can be received by a one-time, continuous, or automated sensor that provides biological data. Biological data can include, for instance, heart rate data, blood oxygen level, respiration level, temperature, or any other data that can provide information concerning drug efficacy or the existence or severity of an adverse reaction. In some embodiments, a predicted tolerance 314 is provided to an output display. The predicted tolerance 314 includes a personalized prediction of tolerance to an adverse drug reaction for a candidate drug at a candidate dosage for a patient. In some embodiments, a recommended dosage 312 is provided to the output display 304. The recommended dosage 312 includes a dosage for a candidate drug that is optimized based upon one or more of real-time efficacy data and/or real-time tolerance data acquired for a patient. The recommended dosage and predicted tolerance can be based, for example, upon data acquired for patients with similar characteristics. In an example, the object may be a hyperlink that directs a web browser to another website.

In exemplary embodiments, a predicted tolerance 314 is provided to a user interface at output 304. In some embodiments, the predicted tolerance 314 is provided with an associated adverse event feature. The predicted tolerance can include qualitative or quantitative data. For example, the predicted tolerance can include a numerical rating on a predetermined scale. In exemplary embodiments, output 304 may simultaneously or sequentially provide several adverse event prediction tolerance ratings and adverse event features. In exemplary embodiments, output 304 may present the user with all available adverse event features and an adverse prediction rating for a candidate drug, drug-drug pair, or drug-patient pair for each feature.

Figure 4:
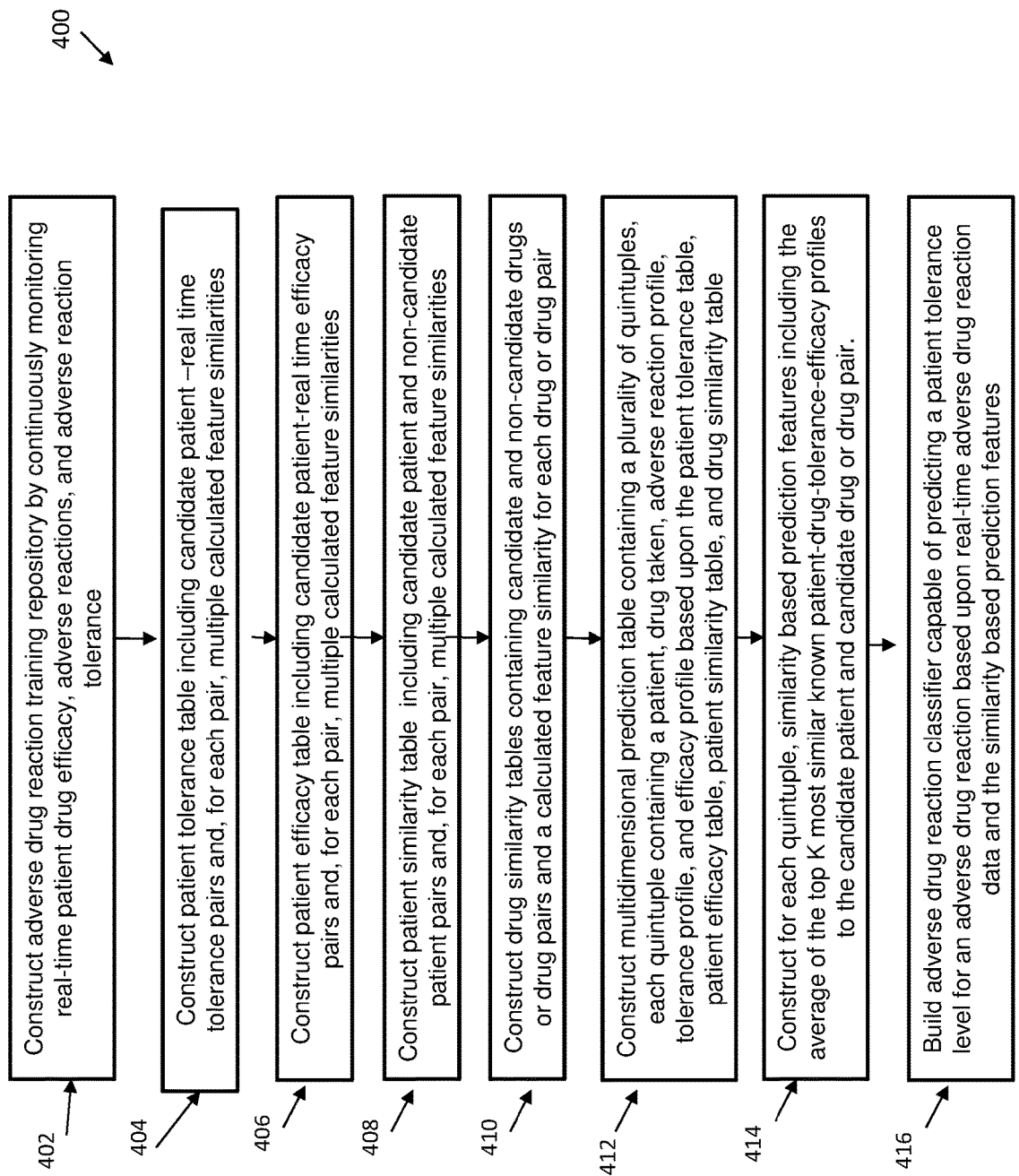
FIG. 4 is a flow diagram of a method for predicting tolerance to adverse events for a candidate patient on a computational system in accordance with one or more embodiments.

Referring now to FIG. 4, a flow diagram of a method 400 for determining an adverse reaction tolerance on a computational system in accordance with one or more embodiments is shown. As shown at block 402, the method 400 includes constructing an adverse drug reaction training repository by continuously monitoring real-time patient drug efficacy, adverse reactions, and adverse reaction tolerance. In another embodiment, a method includes constructing an adverse drug reaction training repository by gathering in real time and/or from historic data, one or more of patient drug efficacy and adverse drug reaction tolerance. In some embodiments, constructing an adverse drug reaction training repository also includes gathering a treatment outcome for a patient. Next as shown at block 404, the method 400 includes constructing patient tolerance tables including candidate patient-real-time tolerance pairs and, for each pair, multiple calculated feature similarities. The method 400 also includes constructing a patient efficacy table including candidate patient-real-time efficacy pairs and, for each pair, multiple calculated feature similarities, as shown at block 406. The method 400 also includes constructing patient similarity tables including candidate patient and non-candidate patient pairs and, for each pair, multiple calculated feature similarities, as shown at block 408. Next, as shown at block 410, the method 400 includes constructing drug similarity tables containing candidate and non-candidate drugs or drug pairs and a calculated feature similarity for each drug or drug pair. The method 400, as shown at block 412, also includes constructing multi-dimensional prediction tables containing a plurality of quintuples, each quintuple containing a patient, drug taken, adverse reaction profile, tolerance profile, and efficacy profile based upon the patient tolerance table, patient efficacy table, patient similarity table, and drug similarity table. Next, as shown at block, 414, the method 400 includes constructing for each quintuple similarity based prediction features including the average of the top K most similar known patient-drug-tolerance-efficacy profiles for the candidate patient and candidate drug or drug pair. Then, as shown at block 416, the method also includes building an adverse drug reaction classifier capable of predicting a patient tolerance level for an adverse drug reaction based upon real-time adverse drug reaction data and the similarity based prediction features.

The disclosure relates to predictions relating to adverse event tolerance concerning various candidates. In exemplary embodiments, predictions can be made regarding adverse event tolerance concerning a candidate drug. For example, predictions can be made concerning the adverse event tolerance predicted to be associated with a candidate drug for a particular patient. In other embodiments, predictions can be made regarding adverse event tolerance concerning a candidate drug-drug pair. For example, predictions can be made concerning the adverse event features predicted to be associated when a patient is administered a certain pair of drugs and the tolerance of a patient to the same. In other embodiments, predictions can be made regarding adverse events concerning a candidate patient-drug pair and the tolerance of a patient to the same. As used herein, candidate patient-drug pair means a candidate drug that is to be administered to a patient with a particular characteristic or medical history. In some embodiments, predictions can be personalized to a particular patient.

As used herein, patient drug tolerance includes information concerning patient willingness to tolerate a given adverse reaction and can depend, in some embodiments, on the drug efficacy and expected treatment outcome.

In some embodiments, the adverse drug reaction training repository includes personalized and known data. For example, in some embodiments, the adverse drug reaction training repository includes personalized and known adverse drug reactions, tolerance level, efficacy and dosage data from a plurality of structured or unstructured data sources. The adverse drug reaction training repository includes, in some embodiments, patient health record data. Preferably, the training repository is organized as a set of multiple datasets. For example, in some embodiments, the training repository includes one or more data sets containing known instances of each type of known adverse drug reaction (e.g., pleading, paralysis, hyperkalemia, etc.) In some embodiments, the training repository includes one or more datasets containing known instances of adverse drug reactions having a particular cause or mechanism (e.g., drug hypersensitivity reactions mediated by IgE, drug-drug combinations that inhibit metabolism of another drug, etc.). In some exemplary embodiments, the training repository includes one or more datasets containing instances of adverse drug reactions with a particular dosage, severity, efficacy or tolerance.

In some embodiments, one or more patient tolerance tables and patient tolerance similarity measures can be constructed. Patient tolerance tables and patient similarity measures can compare patients' reported adverse drug reactions from a variety of perspectives when taking a drug or a combination of drugs. In exemplary embodiments, a patient tolerance table includes candidate or non-candidate drugs or drug pairs, patient tolerance, patient data, and a calculated patient tolerance similarity measure for each drug or drug pair for a patient. For example, in some embodiments, a patient tolerance table can identify a similarity based upon a numerical scale from 0 to 1 (Sim), where 0 is not similar, and 1 is very highly similar, between multiple patients. Similarities can be calculated by any metrics. For example, but not by way of limitation, the calculated similarity can be determined by assessing Cosine similarity, Jaccard/Tanimoto similarity, Pearson correlation, chemical structure similarity metrics, or CPI-based similarity metrics. Preferably, such tables are updated or refined as further information becomes available. For instance, in some embodiments, one or more patient tolerance tables can be continuously updated as real-time information is gathered or collected.

In some embodiments, one or more patient efficacy tables and patient efficacy similarity measures can be constructed. Patient efficacy tables and patient efficacy similarity measures can compare patients' reported efficacy levels from a variety of perspectives when taking a drug or a combination of drugs. In exemplary embodiments, a patient efficacy table includes candidate or non-candidate drugs or drug pairs, patient efficacy, patient data, and a calculated patient efficacy similarity measure for each drug or drug pair for a patient. For example, in some embodiments, a patient tolerance table can identify a similarity based upon a numerical scale from 0 to 1 (Sim), where 0 is not similar, and 1 is very highly similar, between multiple patients.

In some embodiments, one or more multi-dimensional patient profiles and patient similarity measures can be constructed to compare patients from a variety of perspectives. For instance, a patient can be represented by his or her profile including age, gender, race, ethnicity, genomic data, current conditions, prior conditions, and the like. Patient profiles can include health record data, such as any information related to a patient that might be collected by a medical health professional and included in a record. Such information includes, but is not limited to, demographic data, including age, gender, or ethnicity, current medical conditions, prior medical conditions, current symptoms, prior symptoms, height, weight, genomic data, current and prior medications, or current and prior adverse events. Patient similarity measures can be calculated as described above.

In some embodiments, methods include constructing multi-dimensional drug profiles and multiple drug similarity measures. Such profiles and similarity measures can be constructed using one or more structured or unstructured data sources and can include known drug data. Known drug data can include structured data, unstructured data, or both structured and unstructured data. As used herein, structured data includes data that is categorized or grouped in accordance with a system of defined rules. As used herein, unstructured data includes data that is not categorized or grouped in accordance with a system of defined rules. For example, unstructured data includes, but is not limited to, data published in journal articles in a narrative format. In exemplary embodiments, known drug data includes data from databases generally known to persons of ordinary skill in the art. For example, known drug data can include data from the DrugBank database, UniProt, Unified Medical Language System™, PubMed, and/or various scientific journals, including, but not limited to, the Journal of Clinical Oncology, JAMA, BJC, and Clinical Infectious Diseases.

Known drug data can include any information associated with a drug. In exemplary embodiments, known drug data includes feature data and adverse drug event data. For example, known drug feature data includes, but is not limited to, structural data, including for example chemical formula, stereochemistry, chemical structure, crystal structure, primary, secondary, or tertiary protein or peptide structure, nucleotide sequence or confirmation; mechanistic data, including for example mechanism of action; drug metabolism information, including metabolizing enzymes, metabolism pathway; drug physiological effect; drug target; anatomical therapeutic chemical classification; DrugBank category; Chemical-Protein Interactome (CPI) profile. Adverse drug event data includes information related to adverse events associated with a drug. Adverse drug event data can include, for example, the incidence, prevalence, or severity of events such as bleeding, paralysis, and hyperkalemia.

Preferably, the afore-mentioned tables are updated or refined as further information becomes available. For instance, in some embodiments, one or more patient efficacy tables can be continuously updated as real-time information is gathered or collected.

Methods for constructing such tables are known. one or more feature similarity tables can be constructed. In exemplary embodiments, a feature similarity table includes non-candidate drugs or drug pairs and a calculated feature similarity for each drug or drug pair. For example, in some embodiments, a feature similarity table can identify, a similarity based upon a numerical scale from 0 to 1 (Sim), where 0 is not similar, and 1 is very highly similar, between multiple pairs of drugs. For example, a number (N) of feature similarity tables could be related to one of several features numbered 1-N, where N represents a given known feature, such as chemical structure, and may include three columns as follows:

| Sim1 (Chemical Structure) | | |
| --- | --- | --- |
| Drug 1 | Drug 2 | Sim |
| Salsalate | Aspirin | 0.9 |
| Dicoumarol | Warfarin | 0.76 |

| SimN | | |
| --- | --- | --- |
| Drug 1 | Drug 2 | Sim |
| Salsalate | Aspirin | 0.7 |
| Dicoumarol | Warfarin | 0.6 |

Methods of constructing feature tables are known. For instance, in exemplary embodiments, known adverse event feature tables associating adverse events with known drugs or drug pairs can be constructed. In exemplary embodiments, Known Adverse Event Feature Tables for adverse events of type 1 to M can be provided as dual column tables as follows:

| Known Drug Drug Interactions of Type 1 | |
|---|---|
| Drug 1 | Drug 2 |
| Aspirin | Gliclazide |
| Aspirin | Dicoumarol |

| Known Drug Drug Interactions of Type M | |
|---|---|
| Drug 1 | Drug 2 |
| Aspirin | Probenicid |
| Aspirin | Azilsartan |

In exemplary embodiments, multi-dimensional patient-drug-tolerance-efficacy profiles and similarity measures can be constructed. In some embodiments, these profiles and similarity measures compare m patient profiles, m_t patients' real-time tolerance profiles, m_e patients' real-time efficacy profiles, and n set of medications used by the patients. Such profiles can be based upon and can include any of the afore-mentioned tables and profiles.

In exemplary embodiments, a supervised machine learning process (e.g., logistic regression) is performed to determine, from the multi-dimensional patient-drug-tolerance-efficacy profiles and similarity measures, a classifier capable of predicting adverse drug event tolerances. Logistic regression can, in some embodiments, correct for rare events. Logistic regression can be performed, for example, using the multi-dimensional candidate adverse event tolerance tables to create machine learning feature vectors for each candidate.

In some embodiments, additional machine learning features are created to correct for incomplete similarity matrixes. Incomplete similarity matrixes can result, for example, where each one of multiple sources provides data for only a subset of all drugs and drug features considered. For a given candidate with a low similarity based prediction for a drug feature, for example, it can desirable to distinguish between missing information and information that is present but high or low on the similarity scale.

In some embodiments, the method includes building an adverse drug reaction classifier using the real-time personalized adverse drug reaction information and one or more of the real-time patient tolerance information and the real-time efficacy information, such as the adverse event training repository. The adverse drug reaction classifier can, in some embodiments, predict a patient's tolerance level for adverse drug reaction(s). The classifier can be subject, in some embodiments, to a desired efficacy or patient willingness to be subjected to a reaction. In some embodiment, an adverse drug reaction classifier performs a hierarchical classification. For example, an adverse drug reaction classifier can first determine the existence of an interaction or adverse drug reaction and then identify one or more of the nature, cause, severity, tolerance, or efficacy of the prediction.

Figure 5:
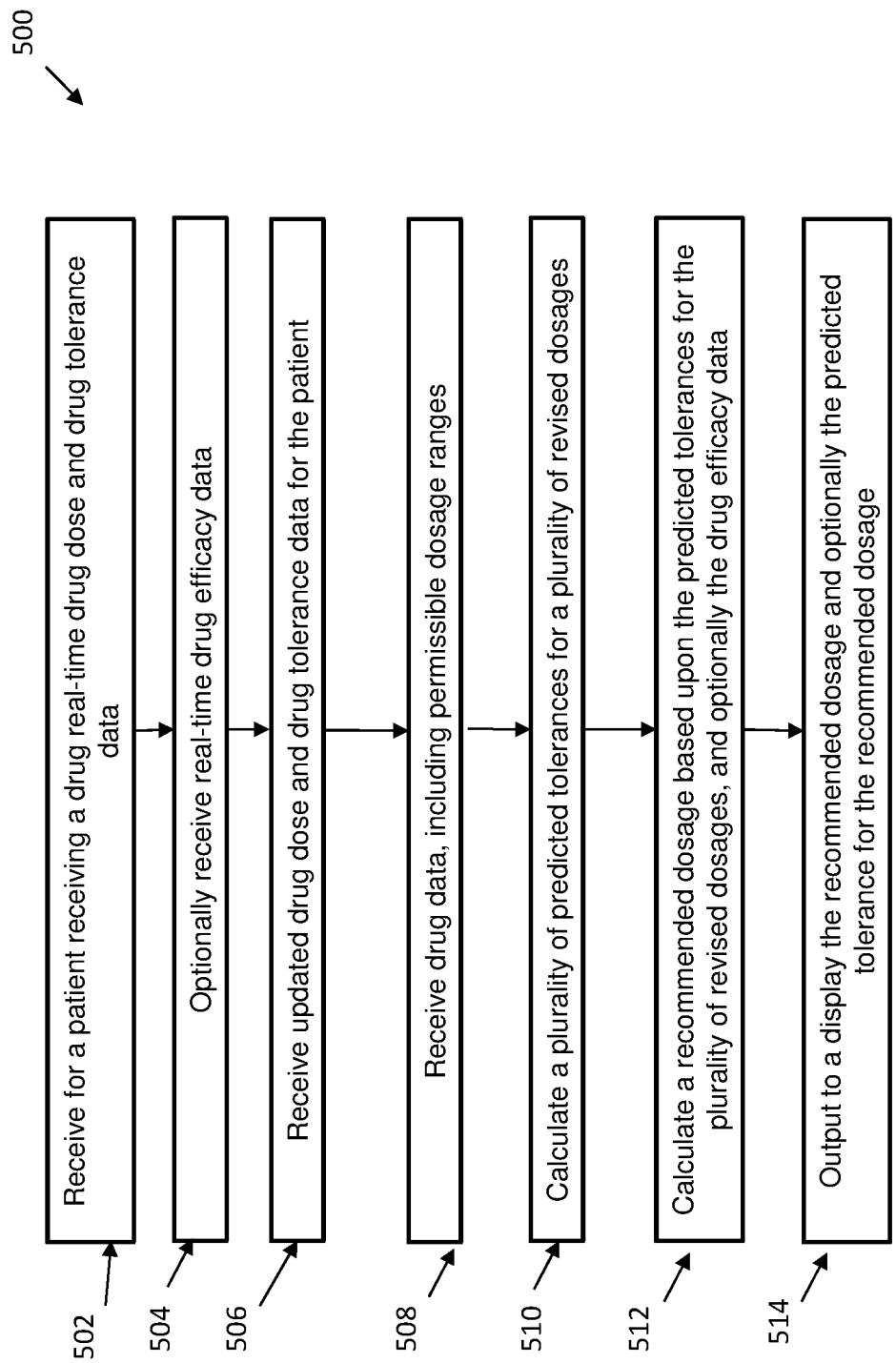
FIG. 5 is a flow diagram of another method for predicting tolerance to adverse events for a candidate patient on a computational system in accordance with one or more embodiments.

Referring now to FIG. 5, a flow diagram of a method 500 for determining an adverse drug reaction tolerance on a computational system in accordance with one or more embodiments is shown. As shown at block 502, the method 500 includes receiving real-time drug dose and drug tolerance data for a patient receiving a drug. Next as shown at block 504, the method 500 optionally includes receiving real-time drug efficacy data. Although FIG. 5 depicts receiving real-time drug dose and drug tolerance data prior to receiving real-time drug efficacy data, it is understood that in some embodiments, drug efficacy data can be received prior to or at the same time as drug efficacy data. As shown at block 506, the method 500 includes receiving updated drug dose and drug tolerance data for the patient. In some embodiments, the data is continuously updated during a period of time in the course of treatment. In some embodiments, data is updated at regular or periodic intervals or at non-periodic intervals. As shown at block 508, the method includes receiving drug data. In some embodiments, the drug data includes permissible drug dosage ranges. The drug data can include known drug data. The method 500 also includes, as shown at block 510, calculating a plurality of predicted tolerances for a plurality of revised dosages. The method 500 also includes calculating a recommended dosage based upon the predicted tolerances for the plurality of revised dosages and optionally the drug efficacy data. Next, as shown at block 514, the method includes outputting the recommended dosage to a display. The method can also optionally including outputting the predicted tolerance for the recommended dosage to a display.

Patient health record data includes any information related to a patient that might be collected by a medical health professional and included in a record. Such information includes, but is not limited to, demographic data, including age, gender, or ethnicity, current medical conditions, prior medical conditions, current symptoms, prior symptoms, height, weight, genomic data, current and prior medications, or current and prior adverse events.

In some embodiments, patient similarity tables are constructed. Patient similarity tables can relate to a feature 1-M, and can contain patient pairs and a calculated patient feature similarity for each patient pair. Patient feature similarities can be calculated by any available means and using known similarity metrics, such as Cosine similarity.

Figure 6:
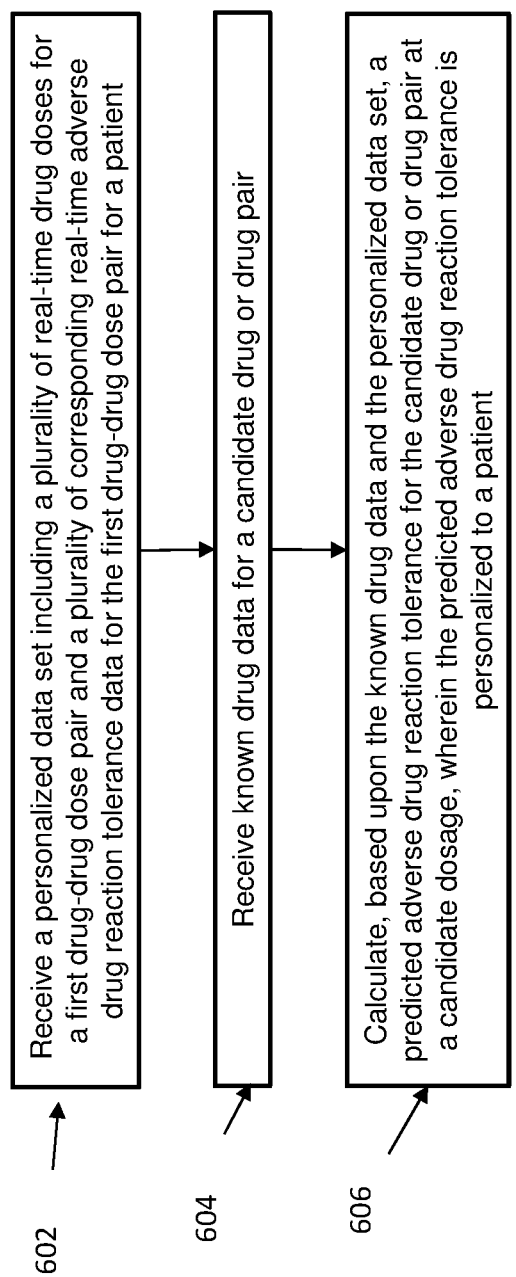
FIG. 6 is a flow diagram of another method for predicting tolerance to adverse events for a candidate patient on a computational system in accordance with one or more embodiments.

Referring now to FIG. 6, a flow diagram of a method 600 for predicting adverse event tolerance is shown. As is shown at block 602, the method 600 includes receiving a personalized data set including a plurality of real-time drug doses for a first drug-dose pair and a plurality of corresponding real-time adverse drug reaction tolerance data for the first-drug-drug dose pair for a patient. Next, the method 600 includes receiving known drug data for a candidate drug or drug pair, as shown in block 604. The method 600 also includes calculating, based upon the known drug data and the personalized data set, a predicted adverse drug reaction tolerance for the candidate drug or drug pair at a candidate dosage, wherein the predicted adverse drug reaction tolerance is personalized to a patient.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may include copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein includes an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which includes one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A computer-implemented method for determining an adverse reaction drug tolerance, the method comprising:

receiving, by a processor, a personalized data set comprising a plurality of real-time drug doses for a first drug or drug combination and a plurality of corresponding real-time adverse drug reaction tolerance data for the first drug or drug combination for a patient, the real-time adverse drug reaction tolerance data comprising a tolerance rating made by the patient that indicates the patient's real-time willingness to tolerate a particular adverse reaction associated with the first drug or drug combination;

receiving, by the processor, known drug data for a candidate drug or drug combination;

constructing a multi-dimensional prediction table containing a plurality of quintuples, each quintuple comprising a known patient, a drug taken, an adverse reaction profile, a tolerance profile, and an efficacy profile;

constructing, for each quintuple, similarity-based prediction features comprising an average of a top K most similar known patient-drug-tolerance-efficacy profiles for the patient and the candidate drug or drug combination;

calculating, by the processor, based upon the known drug data, the personalized data set, and the similarity-based prediction features, a predicted adverse drug reaction tolerance for the candidate drug or drug combination at a candidate dosage, wherein the predicted adverse drug reaction tolerance is personalized to the patient; calculating a recommended dosage for the candidate drug or drug combination based upon the predicted adverse drug reaction tolerance; and the known drug data, and outputting the recommended dosage to a display.

2. The computer-implemented method of claim 1, the method further comprising receiving, to the processor, real-time drug efficacy data for the patient.

3. The computer-implemented method of claim 1, comprising continuously monitoring a drug tolerance for the patient.

4. The computer-implemented method of claim 1, comprising constructing a multi-dimensional patient tolerance table comprising a plurality of patient-real time tolerance data pairs and, for each of the patient-real time tolerance data pairs, one or more calculated feature similarities.

5. The computer-implemented method of claim 1, comprising constructing a multi-dimensional patient efficacy table comprising a plurality of patient-real time efficacy data pairs and, for each of the patient-real time efficacy data pairs, one or more calculated feature similarities.

6. The computer-implemented method of claim 1, the method further comprising outputting to a display a classification of the predicted adverse event tolerance, the classification comprising one or more of a nature, a cause, a severity, a tolerance, or an efficacy associated with the predicted adverse event tolerance.

7. A computer program product for calculating an adverse reaction drug tolerance on a computational system, the computer program product comprising:

A non-transitory computer readable storage medium having program instructions embodied therewith, the program instructions executable by a processor to cause the processor to:

receive a personalized data set comprising a plurality of real-time drug doses for a first drug or drug combination and a plurality of corresponding real-time adverse drug reaction tolerance data for the first drug or drug combination for a patient, the real-time adverse drug reaction tolerance data comprising a tolerance rating made by the patient that indicates the patient's real-time willingness to tolerate a particular adverse reaction associated with the first drug or drug combination;

receive known drug data for a candidate drug or drug combination;

construct a multi-dimensional prediction table containing a plurality of quintuples, each quintuple comprising a known patient, a drug taken, an adverse reaction profile, a tolerance profile, and an efficacy profile;

construct, for each quintuple, similarity-based prediction features comprising an average of a top K most similar known patient-drug-tolerance-efficacy profiles for the patient and the candidate drug or drug combination;

calculate, based upon the known drug data and the personalized data set, and the similarity-based prediction features, a predicted adverse drug reaction tolerance for the candidate drug or drug combination at a candidate dosage, wherein the predicted adverse drug reaction tolerance is personalized to the patient; calculating a recommended dosage for the candidate drug or drug combination based upon the predicted adverse drug reaction tolerance; and the known drug data, and outputting the recommended dosage to a display.

8. The computer program product of claim 7, wherein the method further comprises receiving real-time drug efficacy data for the patient.

9. The computer program product of claim 7, wherein the method comprises continuously monitoring a drug tolerance for the patient.

10. The computer program product of claim 7, wherein the known drug data comprises known adverse drug reaction data from a structured or unstructured data source.

11. The computer program product of claim 6, wherein the known drug data comprises a patient health record.

12. The computer program product of claim 6, wherein the method comprises constructing a multi-dimensional patient tolerance table comprising a plurality of patient-real time tolerance data pairs and, for each of the patient-real time tolerance data pairs, one or more calculated feature similarities.

13. The computer program product of claim 6, wherein the method comprises constructing a multi-dimensional patient efficacy table comprising a plurality of patient-real time efficacy data pairs and, for each of the patient-real time efficacy data pairs, one or more calculated feature similarities.

14. A processing system for calculating an adverse reaction drug tolerance on a computational system, comprising:

a processor in communication with one or more types of memory, the processor configured to:

receive a personalized data set comprising a plurality of real-time drug doses for a first drug or drug combination and a plurality of corresponding real-time adverse drug reaction tolerance data for the first drug or drug combination for a patient, the real-time adverse drug reaction tolerance data comprising a tolerance rating made by the patient that indicates the patient's real-time willingness to tolerate a particular adverse reaction associated with the first drug or drug combination;

receive known drug data for a candidate drug or drug combination;

construct a multi-dimensional prediction table containing a plurality of quintuples, each quintuple comprising a known patient, a drug taken, an adverse reaction profile, a tolerance profile, and an efficacy profile;

construct, for each quintuple, similarity-based prediction features comprising an average of a top K most similar known patient-drug-tolerance-efficacy profiles for the patient and the candidate drug or drug combination;

calculate, based upon the known drug data, the personalized data set, and the similarity-based prediction features, a predicted adverse drug reaction tolerance for the candidate drug or drug combination at a candidate dosage, wherein the predicted adverse drug reaction tolerance is personalized to the patient; calculating a recommended dosage for the candidate drug or drug combination based upon the predicted adverse drug reaction tolerance; and the known drug data, and outputting the recommended dosage to a display.

15. The processing system of claim 14, wherein the processor is configured to receive real-time drug efficacy data for the patient.

16. The processing system of claim 14, wherein the processor is configured to construct a multi-dimensional patient tolerance table comprising a plurality of patient-real time tolerance data pairs and, for each of the patient-real time tolerance data pairs, one or more calculated feature similarities.

17. The processing system of claim 14, wherein the processor is configured to construct a multi-dimensional patient efficacy table comprising a plurality of patient-real time efficacy data pairs and, for each of the patient-real time efficacy data pairs, one or more calculated feature similarities.

18. The processing system of claim 14, wherein the processor is configured to construct one or more multi-dimensional drug profiles including multiple adverse event features for the candidate drug or drug combination.

* * * * *